United States Patent [19]

Hagiwara et al.

[11] Patent Number: 5,310,926
[45] Date of Patent: May 10, 1994

[54] PROCESS FOR PRODUCING ISOXAZOLE DERIVATIVES

[75] Inventors: Yu-ichi Hagiwara, Iruma; Motoaki Tanaka, Tokorozawa; Makoto Kajitani, Hidaka; Mitsugi Yasumoto, Honjo, all of Japan

[73] Assignee: Taiho Pharmaceutical Co., Limited, Tokyo, Japan

[21] Appl. No.: 121,557

[22] Filed: Sep. 16, 1993

Related U.S. Application Data

[62] Division of Ser. No. 761,826, Sep. 12, 1991.

[30] Foreign Application Priority Data

Jan. 24, 1990 [JP] Japan .................. 2-14239

[51] Int. Cl.$^5$ .............................. C07D 261/08
[52] U.S. Cl. ................................. 548/247
[58] Field of Search .......................... 548/247

[56] References Cited

U.S. PATENT DOCUMENTS

5,142,091 4/1992 Tanaka et al. .................. 558/405

OTHER PUBLICATIONS

CA 110(21):192690j Synthesis ... acid. Yamawaki et al., p. 737, 1989.
CA 113(13):108936a General ... drug. Effect ... system. Yamamoto et al., p. 39, 1990.
CA 114(5):42776k Preparation ... isoxazolylacetates, Hagiwara et al., p. 744, 1991.

*Primary Examiner*—Mary C. Lee
*Assistant Examiner*—Joseph K. McKane
*Attorney, Agent, or Firm*—Nikaido, Marmelstein, Murray & Oram

[57] ABSTRACT

The present invention provides a process for producing isoxazole derivatives represented by the formula

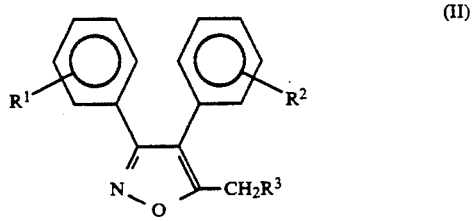

(II)

wherein $R^1$ and $R^2$ are the same or different and are each a hydrogen atom or lower alkoxyl, and $R^3$ is cyano or alkoxycarbonyl, the process being characterized by oxidizing an $\alpha, \beta$-unsaturated ketoxime derivative represented by the formula

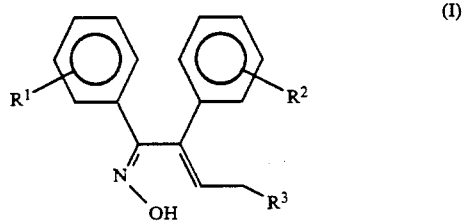

(I)

wherein $R^1$, $R^2$ and $R^3$ are as defined above.

The isoxazole derivatives (II) to be produced by the process of the present invention are useful as intermediates for preparing (3,4-diarylisoxazol-5-yl) acetic acid derivatives which are useful as anti-inflammatory agents, analgesics and antipyretics.

3 Claims, No Drawings

PROCESS FOR PRODUCING ISOXAZOLE DERIVATIVES

This is a division of application Ser. No. 07/761,826, filed Sep. 12, 1991.

TECHNICAL FIELD

The present invention relates to a process for industrially advantageously producing isoxazole derivatives represented by the formula

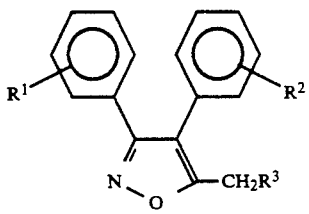

wherein $R^1$ and $R^2$ are the same or different and are each a hydrogen atom or lower alkoxyl, and $R^3$ is cyano or alkoxycarbonyl.

The isoxazole derivatives to be produced by the process of the present invention are useful as intermediates for preparing (3,4-diarylisoxazol-5-yl) acetic acid derivatives which are represented by the formula

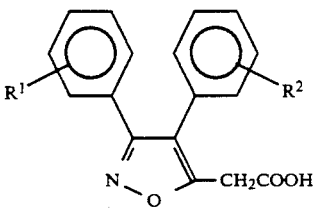

wherein $R^1$ and $R^2$ are the same or different and are each a hydrogen atom or lower alkoxyl, and which are useful as antiinflammatory agents, analgesics and antipyretics.

BACKGROUND ART

Among the isoxazole derivatives represented by the formula (II), the compounds wherein $R^3$ is cyano are prepared by the known process which is disclosed in JP-A-75471/1985. This process comprises reacting 3,4-diaryl-5-methylisoxazole with a halogenating agent and then with a cyanogenation agent. The compounds of the formula wherein $R^3$ is alkoxycarbonyl are novel compounds.

An object of the present invention is to provide a novel and preferred process, which is entirely different from the conventional process, for producing isoxazole derivatives represented by formula (II) and useful as intermediates for preparing the compounds (A).

DISCLOSURE OF THE INVENTION

The present invention provides a process for producing isoxazole derivatives represented by the formula

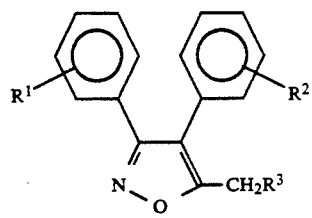

wherein $R^1$ and $R^2$ are the same or different and are each a hydrogen atom or lower alkoxyl, and $R^3$ is cyano or alkoxycarbonyl, the process being characterized by oxidizing an α, β-unsaturated ketoxime derivative represented by the formula

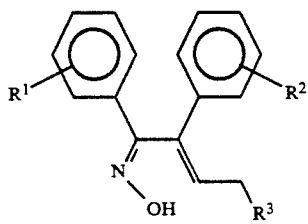

wherein $R^1$, $R^2$ and $R^3$ are as defined above.

According to the present invention, preferred examples of lower alkoxyl groups represented by $R^1$ and $R^2$ are straight-chain or branched-chain alkoxyl groups having 1 to 6 carbon atoms, such as methoxy, ethoxy, n-propoxy, isopropoxy, n-butoxy, isobutoxy, sec-butoxy, tert-butoxy, pentyloxy and hexyloxy. Examples of alkoxycarbonyl groups represented by $R^3$ are straight-chain or branched-chain alkoxycarbonyl groups having 2 to 7 carbon atoms, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl and hexyloxycarbonyl.

The isoxazole derivatives to be produced by the process of the invention are useful as intermediates for preparing (3,4-diarylisoxazol-5-yl)acetic acid derivatives which are useful as anti-inflammatory agents, analgesics and antipyretics and which are represented by the formula

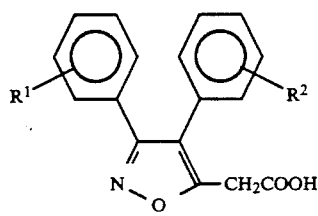

wherein $R^1$ and $R^2$ are the same or different and are each a hydrogen atom or lower alkoxyl.

The compound (1) for use in the present invention is prepared, for example, in accordance with the following reaction scheme.

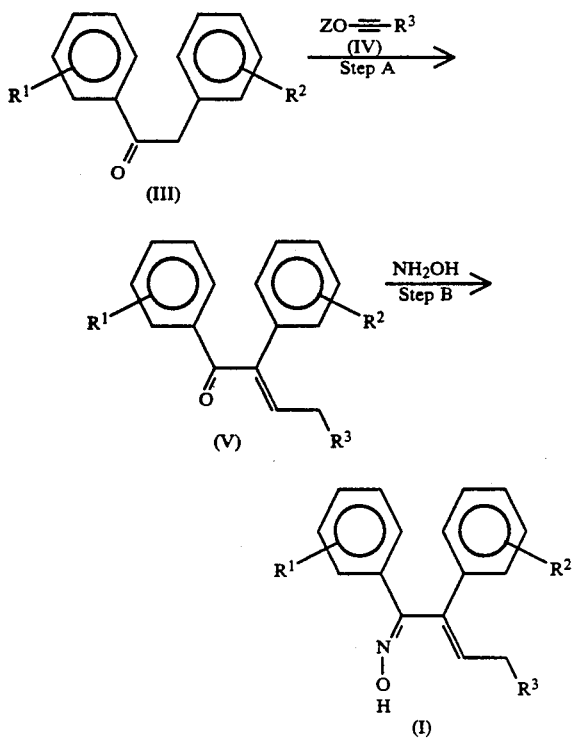

wherein $R^1$, $R^2$ and $R^3$ are as defined above, and Z is lower alkyl.

Examples of lower alkyl groups represented by Z in the above scheme are straight-chain or branched-chain alkyl groups having 1 to 6 carbon atoms, such as methyl, ethyl, n-propyl, isopropyl, n-butyl, sec-butyl, tert-butyl, pentyl and hexyl.

More specifically, the steps represented by the above reaction scheme are performed in the following manner.

Step A

A deoxybenzoin derivative represented by the formula (III) is reacted with an alkoxyacrylonitrile or alkoxyacrylic acid derivative represented by the formula (IV) in a suitable solvent in the presence of a base to obtain a compound of the formula (V). The solvent is not limited specifically insofar as it does not participate in the reaction. Examples of useful solvents are various organic solvents including methanol, ethanol, tert-butanol and like alcohols, tetrahydrofuran, dioxane and like ethers, benzene, toluene, xylene and like aromatic hydrocarbons, carbon tetrachloride, chloroform, dichloromethane and like hydrocarbon halides, acetonitrile, pyridine, dimethylformamide, etc. These solvents can be used singly or in admixture. Examples of useful bases are sodium hydroxide, sodium methoxide, potassium tert-butoxide, butyl lithium and like alkali bases, triethylamine, dimethylaminopyridine and like organic bases, etc. For the reaction, it is desirable to use 1 to 3 moles of the compound of the formula (IV) per mole of the compound of the formula (III), and 0.1 to 3 moles of the base per mole of the compound of the formula (III). The reaction is conducted at a temperature of up to 200° C., preferably from 0° C. approximately to the boiling point of the solvent. The reaction usually takes about 0.5 to about 20 hours for completion.

Step B

The compound represented by the formula (V) and obtained by step A is reacted with hydroxylamine or a salt thereof in a suitable solvent to thereby obtain a compound represented by the formula (I). The salt of hydoxylamine to be used for the reaction is not limited specifically and is, for example, the hydrochloric acid salt, sulfuric acid salt or the like. The solvent is not limited specifically insofar as it does not participate in the reaction. Examples of useful solvents are various organic solvents including methanol, ethanol, tert-butanol and like alcohols, tetrahydrofuran, dioxane and like ethers, benzene, toluene, xylene and like aromatic hydrocarbons, carbon tetrachloride, chloroform, dichloromethane and like hydrocarbon halides, acetonitrile, pyridine, dimethylformamide, etc. These solvents can be used singly or in admixture. For the reaction, it is desirable to use 1 to 10 moles of hydroxylamine or a salt thereof per mole of the compound of the formula (V). The reaction is conducted at a temperature of 0° to 200° C., preferably from 40° C. approximately to the boiling point of the solvent. The completion of the reaction usually takes about 1 to about 30 hours.

The process of the invention for producing an isoxazole derivative represented by the formula (II) is characterized by oxidizing the compound of the formula (I) obtained according to the above reaction scheme. More specifically, the present invention resides in reacting the compound of the formula (I) with an oxidizing agent in a suitable solvent or in the absence of any solvent.

The oxidation process to be employed in the present invention is, for example, a process disclosed in "Lectures on New Experimental Chemistry," Vol. 15, I -1, I -2, "Oxidation and Reduction," edited by the Chemical Society of Japan, published by Maruzen Co., Ltd. Examples of useful processes are a process using an oxidizing reagent such as potassium permanganate, manganese dioxide, potassium periodate, sodium periodate, ruthenium tetroxide or like oxide, lead tetracetate, mercury acetate, iron (III) chloride, potassium hexacyanoferrate (III) or like metal salt, hydrogen peroxide solution, peracetic acid or like peroxide, or the like, an autoxidation process using air or oxygen, an organic electrolytic oxidation process utilizing anodic oxidation, etc.

For the reaction wherein the oxidizing reagent is used, it is desirable to use 0.2 to 10 moles of the reagent per mole of the compound of the formula (I). The solvent is not limited specifically insofar as it does not participate in the reaction. Examples of useful solvents are various organic solvents such as dichloromethane, chloroform, carbon tetrachloride and like hydrocarbon halides, benzene, toluene and like aromatic hydrocarbons, methanol, ethanol and like alcohols, diethyl ether, tetrahydrofuran and like ethers, acetone, hexane, acetic acid, etc. These solvents can be used singly, in admixture or as admixed with water. The reaction temperature is −20° to 100° C., preferably 5° to 70° C. The completion of the reaction usually takes about 5 minutes to about 10 hours. When required, the reaction may be conducted with addition of an acid or base, or in a solvent mixture including a buffer or the like.

The autoxidation process and the organic electrolytic oxidation process are conducted by passing air, oxygen or current through the reaction system in a suitable solvent. The solvent is not limited specifically insofar as it does not participate in the reaction. Examples of useful solvents are various organic solvents such as dichloromethane, chloroform, carbon tetrachloride and like hydrocarbon halides, benzene, toluene and like aromatic hydrocarbons, methanol, ethanol and like alcohols, diethyl ether, tetrahydrofuran and like ethers, acetone, hexane, acetic acid and the like. These solvents can be used singly, in admixture, or as mixed with water. The reaction temperature is −20° to 100° C., preferably 5° to 70° C. The completion of the reaction usually takes about 5 minutes to about 24 hours. It is known that the reaction proceeds generally efficiently in the presence of a catalyst. Preferably, the catalyst is used in an amount of $1 \times 10^{-5}$ to 10 moles per mole of the compound of the formula (I). Although the catalyst is not limited specifically, examples of useful catalysts are metals such as cobalt, rhodium, palladium, copper, cerium and ruthenium, or salts, oxides, complexes or like compounds of such metals. When required, the reaction may be conducted with addition of an acid or base, or in a solvent mixture including a buffer or the like.

The compound of the invention thus obtained can be isolated and purified by usual known methods, for example, by distillation, recrystallization or silica gel column chromatography.

The isoxazole compound represented by the formula (II) and prepared by the above process is subjected, as isolated or as it is without isolation, to solvolysis or to hydrolysis in the presence of an acid or base, whereby a (3,4-diarylisoxazol-5-yl)acetic acid derivative represented by the formula (A) and having anti-inflammatory and analgesic activities can be derived from the compound of the invention. The solvolysis or hydrolysis can be conducted by solvolysis process disclosed in JP-A-75471/1985 or by the hydrolysis process generally employed in the art concerned. Generally used as the acid is an inorganic acid such as hydrochloric acid, sulfuric acid or nitric acid, or as the base is an inorganic base such as sodium hydroxide, potassium hydroxide or sodium carbonate.

BEST MODE OF CARRYING OUT THE INVENTION

The present invention will be described below in detail with reference to reference examples and examples.

REFERENCE EXAMPLE 1

Preparation of methyl 4,5-bis(4-methoxyphenyl)-5-oxo-3-pentenoate

To 430 ml of tert-butanol were added 128 g of deoxyanisoin, 67.3 g of potassium tert-butoxide and 116 g of methyl 3-methoxyacrylate, and the mixture was stirred at 70° C. for 3 hours. After the completion of reaction, the reaction mixture was allowed to stand at room temperature with addition of n-hexane. The product separating out was filtered off and dissolved with 1000 ml of ethyl acetate and 300 ml of 3N sulfuric acid. The organic layer was collected, washed with 3N sulfuric acid and a saturated aqueous solution of sodium chloride, and dried over anhydrous magnesium sulfate. The organic layer was concentrated at a reduced pressure, giving 153 g (yield 90%) of the above-identified compound as an oily product.

An NMR spectrum revealed that the compound was a mixture of isomers (about 6:4) due to a double bond. The mixture was recrystallized from hexane-ethyl acetate as required, whereby one of the isomers was isolated in the form of white crystals.

Melting point 101°~103° C.

IR absorption spectrum (KBr): $\nu$max (cm$^{-1}$): 1732, 1640, 1600.

NMR spectrum (CDCl$_3$) δ (ppm): 3.31 (2H, d), 3.72 (3H, s), 3.80 (3H, s), 3.85 (3H, s), 6.37 (1H, t), 6.90 (4H, d), 7.23 (2H, d), 7.89 (2H, d).

The mother liquor further gave the other isomer of the compound in the form of an oily product.

IR absorption spectrum (KBr) $\nu$max (cm$^{-1}$) 1732, 1662, 1596.

NMR spectrum (CDCl$_3$) δ (ppm) 3.15 (2H, d), 3.65 (3H, s), 3.77 (3H, s), 3.83 (3H, s), 6.30 (1H, t), 6.6~7.1 (4H, m), 7.30 (2H, d), 7.92 (2H, d).

REFERENCE EXAMPLE 2

Preparation of 4,5-bis(4-methoxyphenyl)-5-oxo-3-pentenenitrile

The identified compound was obtained as an oily product by conducting the same reaction as in Reference Example 1 with the exception of using 3-methoxyacrylonitrile instead of methyl 3-methoxyacrylate.

IR absorption spectrum (NaCl): $\nu$max (cm$^{-1}$) 2250, 1660, 1606.

NMR spectrum (CDCl$_3$) δ (ppm) 3.17 (2H, d), 3.78 (3H, s), 3.85 (3H, s), 6.03 (3H, t), 6.7~7.0 (4H, m), 7.27 (2H, d), 7.90 (2H, d).

REFERENCE EXAMPLE 3

Preparation of methyl 5-hydroxyimino-4,5-bis(4-methoxyphenyl)-3-pentenoate

The isomer mixture of 4,5-bis(4-methoxyphenyl)-5-oxo-3-pentenoate (24.5 g) obtained in Reference Example 1 and 51.5 g of hydroxylamine hydrochloride was heated under reflux in a mixture of 650 ml of methanol and 72 ml of water for 23 hours. With the progress of reaction at this time, 0.9 equivalent weight of sodium hydrogencarbonate was added in divided portions to the reaction system. On completion of the reaction, the methanol was distilled off at a reduced pressure. The residue was dissolved with water and ethyl acetate, and the organic layer was collected, washed with a saturated aqueous solution of sodium chloride and dried over anhydrous magnesium sulfate. The organic layer was concentrated at a reduced pressure, and the residue was subjected to silica gel column chromatography (eluants: ethyl acetate-n-hexane) for separation and purification, affording 23 g (yield 90%) of the above-identified compound as an oily product.

IR absorption spectrum (NaCl): $\nu$max (cm$^{-1}$) 1732, 1608.

NMR spectrum (CDCl$_3$) δ (ppm) 3.1~3.2 (2H, m), 3.65 (3H, s), 3.76 (3H, s), 3.77 (3H, s), 6.48 (1H, t), 6.81 (4H, d), 7.35 (2H, d), 7.58 (4H, d), 8.72 (1H, bs).

REFERENCE EXAMPLE 4

Preparation of 5-hydroxyimino-4,5-bis(4-methoxyphenyl)-3-pentenenitrile

The identified compound was prepared as an oily product by conducting the same reaction as in Reference Example 3 with the exception of using 4,5-bis(4-methoxyphenyl)-5-oxo-3-penteneitrile in place of 4,5-bis(4-methoxyphenyl)-5-oxo-3-pentenoate.

IR spectrum (NaCl): $\nu$max (cm$^{-1}$) 2252, 1596.

NMR spectrum (CDCl$_3$) δ (ppm): 3.12, 3.15 (2H, dd), 3.77 (3H, s), 3.78 (3H, s), 6.18 (1H, t), 6.84 (4H, d), 7.32 (2H, d), 7.55 (2H, d), 8.46 (1H, bs).

EXAMPLE 1

Preparation of 5-methoxycarbonylmethyl-3,4-bis(4-methoxyphenyl)isoxazole (II a)

A 3.7 g quantity of methyl 5-hydroxyimino-4,5-bis(4-methoxyphenyl)-3-pentenoate was heated at 60° C. with stirring for 24 hours in 40 ml of acetic acid in the presence of 0.4 g of cobalt acetate tetrahydrate while passing air through the mixture. After addition of 3N sulfuric acid, the reaction mixture was subjected to extraction with ethyl acetate, and the organic layer was washed with a saturated solution of potassium carbonate and then with a saturated aqueous solution of sodium chloride and dried over anhydrous magnesium sulfate. The organic layer was concentrated at a reduced pressure, and the residue was subjected to silica gel column chromatography (eluants: ethyl acetate-n-hexane) for separation and purification, giving 3.3 g (yield 90%) of the above-identified compound as a while solid product.

Melting point 67°~68° C.

IR absorption spectrum (KBr) $\nu$max (cm$^{-1}$) 1730.

NMR spectrum (CDCl$_3$) δ (ppm) 3.73 (3H, s), 3.77 (2H, s), 3.79 (3H, s), 3.82 (3H, s), 6.83 (2H, d), 6.90 (2H, d), 7.15 (2H, d), 7.40 (2H, d).

Mass spectrum: M+ (m/z) 353.

EXAMPLE 2

Preparation of 5-cyanomethyl-3,4-bis(4-methoxyphenyl)isoxazole (II b)

The identified compound was obtained as a white solid product (yield 80%) in the same manner as in Example 1 with the exception of using 5-hydroxyimino-4,5-bis(4-methoxyphenyl)-3-pentenenitrile in place of methyl 5-hydroxyimino-4,5-bis(4-methoxyphenyl)-3-pentenoate.

Melting point 103°~104° C.

IR absorption spectrum (KBr): $\nu$max (cm$^{-1}$) 2264.

NMR spectrum (CDCl$_3$) δ (ppm): 3.80 (3H, s), 3.83 (2H, s), 3.85 (3H, s), 6.8~7.5 (8H, m).

Mass spectrum: M+ (m/z) 320

A 1.77 g quantity of the 5-methoxycarbonylmethyl-3,4-bis(4-methoxyphenyl)isoxazole (II a) obtained in Example 1 was added to 15 ml of 2% aqueous solution of sodium hydroxide, followed by stirring at 40° C. overnight. After the completion of reaction, the reaction mixture was washed with ether twice. While cooling the mixture with ice, 5 ml of 10% hydrochloric acid was subsequently added thereto, followed by extraction with ethyl acetate, then washing with a saturated aqueous solution of sodium chloride and thereafter drying over anhydrous magnesium sulfate. The organic layer was concentrated at a reduced pressure, giving 3,4-bis(4-methoxyphenyl)-isoxazol-5-acetic acid as a white solid product (melting at 147°~148° C.).

EXAMPLE 3

Preparation of 5-methoxycarbonylmethyl-3,4-bis(4-methoxyphenyl)isoxazole (II a)

A 1.75 g (5 mmols) quantity of methyl 5-hydroxyimino-4,5-bis(4-methoxyphenyl)-3-pentenoate was dissolved in 8.5 ml of dichloromethane and 4 ml of acetic acid, then 0.79 g of potassium permanganate was slowly added to the solution at room temperature, and the mixture was stirred for 4 hours. After the completion of reaction, a hydrogen peroxide solution was added to the reaction mixture until the mixture became transparent. The mixture was diluted with 10 ml of dichloromethane, subsequently washed with water, with sodium hydrogencarbonate and with a saturated aqueous solution of sodium chloride successively, and dried over anhydrous magnesium sulfate. The dried product was subjected to silica gel column chromatography (eluants: ethyl acetate-n-hexane) for separation and purification, affording 10.2 g (yield 60%) of the above-identified compound as a white solid product.

The melting point, IR absorption spectrum and NMR spectrum of the product coincided with those of the compound obtained in Example 1.

EXAMPLE 4

Preparation of 5-methoxycarbonylmethyl-3,4-bis(4-methoxyphenyl)isoxazole (IIa)

A 1.2 g (3.38 mmols) quantity of methyl 5-hydroxyimino-4,5-bis(4-methoxyphenyl)-3-pentenoate was dissolved in 19 ml of acetic acid, and the solution was added dropwise to a suspension composed of 0.44 g (5.1 mmols) of manganese dioxide and 5 ml of acetic acid at 60° C. After the completion of addition, the mixture was stirred at 60° C. for one hour. After the completion of reaction, hydrogen peroxide was added to the reaction mixture to decompose excess manganese dioxide. The same procedure as in Example 3 was thereafter repeated to obtain 0.78 g (yield 65%) of the above-identified product.

The melting point, IR absorption spectrum and NMR spectrum of the product coincided with those of the compound obtained in Example 1.

Industrial Applicability

The isoxazole derivative produced by the process of the invention is useful as an intermediate for preparing a (3,4-diarylisoxazol-5-yl)acetic acid derivative which is useful as an anti-inflammatory agent, analgesic and antipyretic and which is represented by the formula (A)

wherein R$^1$ and R$^2$ are the same or different and are each a hydrogen atom or lower alkoxyl.

We claim:

1. A process for producing an isoxazole derivative of the formula (II):

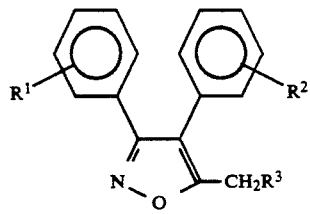

wherein $R^1$ and $R^2$ are the same or different and are each a hydrogen atom or lower alkoxy and $R^3$ is cyano or alkoxycarbonyl, comprising the steps of a) reacting a desoxybenzoin derivative of the formula (III)

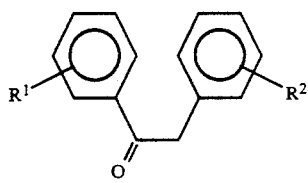

with an alkoxyacrylonitrile or alkoxyacrylic acid derivative of the formula (IV)

wherein Z is a lower alkyl, in a suitable solvent in the presence of a base to produce a compound of the formula (V)

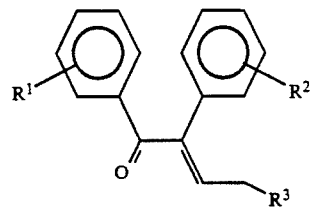

b) then reacting the resulting compound of the formula (V) with hydroxylamine or a salt thereof in a suitable solvent at a temperature of 0° to 200° C. to obtain an α, β unsaturated ketoxime derivative of the formula (I)

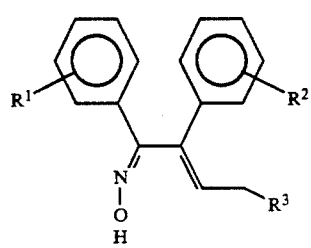

wherein $R^1$, $R^2$, and $R^3$ are as defined above, and c) oxidizing the compound of the formula (I).

2. The process according to claim 1, wherein $R^1$ and $R^2$ are each lower alkoxy groups.

3. The process according to claim 1, wherein the oxidizing step is conducted by a process using an oxidizing reagent selected from the group consisting of potassium permanganate, manganese dioxide, potassium periodate, sodium periodate, ruthenium tetroxide, lead tetraacetate, mercury acetate, iron (III) chloride, potassium hexacyanoferrate (III), hydrogen peroxide solution or peracetic acid, an autoxidation process using air or oxygen, and an organic electrolytic oxidation process utilizing anodic oxidation.

* * * * *